United States Patent
Yamaguchi et al.

(10) Patent No.: US 6,897,958 B2
(45) Date of Patent: May 24, 2005

(54) APPARATUS AND METHOD FOR INSPECTING LIGHT TRANSMITTABLE MATERIAL

(75) Inventors: Yukihiko Yamaguchi, Kanagawa (JP); Koichi Murai, Kanagawa (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 297 days.

(21) Appl. No.: 10/122,336

(22) Filed: Apr. 16, 2002

(65) Prior Publication Data

US 2002/0149771 A1 Oct. 17, 2002

(30) Foreign Application Priority Data

Apr. 17, 2001 (JP) ........................................ 2001-118379

(51) Int. Cl.$^7$ .............................................. G01N 21/896
(52) U.S. Cl. ................... 356/431; 356/443; 250/559.02
(58) Field of Search ............................. 356/239.1, 431, 356/445, 443, 435; 250/559.02

(56) References Cited

U.S. PATENT DOCUMENTS

| | | | | |
|---|---|---|---|---|
| 3,768,905 A | * | 10/1973 | Williams ...................... | 355/77 |
| 4,577,961 A | * | 3/1986 | Terashita ...................... | 355/77 |
| 4,646,252 A | * | 2/1987 | Terashita ...................... | 356/404 |
| 4,650,316 A | * | 3/1987 | Matsumoto ................... | 355/55 |
| 4,972,091 A | * | 11/1990 | Cielo et al. .............. | 250/559.18 |
| 5,266,805 A | * | 11/1993 | Edgar .......................... | 250/330 |
| 5,365,075 A | * | 11/1994 | Peterson ................. | 250/559.02 |
| 5,775,627 A | * | 7/1998 | Murakami ................... | 242/526 |
| 5,969,372 A | * | 10/1999 | Stavely et al. .......... | 250/559.42 |
| 5,995,197 A | * | 11/1999 | Yoshino ....................... | 355/41 |
| 6,064,478 A | * | 5/2000 | Paul et al. ................ | 356/237.1 |
| 6,512,238 B1 | * | 1/2003 | Iwaki ..................... | 250/559.02 |
| 6,552,778 B1 | * | 4/2003 | Konagaya ................... | 382/275 |

FOREIGN PATENT DOCUMENTS

| DE | 199 19 895 | * 11/2000 | .......... G01N/21/89 |
|---|---|---|---|

* cited by examiner

*Primary Examiner*—Zandra Smith
*Assistant Examiner*—Kara Geisel
(74) *Attorney, Agent, or Firm*—Sughrue Mion, PLLC

(57) ABSTRACT

In an inspection device, an inspection light projector and an auxiliary light emitter respectively project an inspection light and auxiliary light onto a position of a filmstrip. After transmitting the filmstrip, the inspection light is received by a defect detector. When receiving the inspection light, the defect detector generates a data signal and sends it to a controller. In the controller, a threshold of a level of the data signal is memorized, and the level of the data signal is compared with the threshold. If the level of the data signal becomes under the threshold, the controller determines that the filmstrip has a coloring defect. Further, if there is a dust on the filmstrip, the level of the data signal becomes higher. Because the auxiliary light is diffused by the dust, and a part of the auxiliary light is received by the defect detector.

17 Claims, 8 Drawing Sheets

APPARATUS AND METHOD FOR INSPECTING LIGHT TRANSMITTABLE MATERIAL

BACKGROUND OF THE INVENTION

1. Field of the Invention

The present invention relates to an apparatus and a method for inspecting a light transmittable material, such as a filmstrip, to detect a defect thereon.

2. Description Related to the Prior Art

In producing a filmstrip including cyan, magenta and yellow coloring layers, the filmstrip is examined. At the end of the examination, an unexposed filmstrip is developed as a sample film for determining whether there is a defect of optical sensitization (or a coloring defect) on the filmstrip. The coloring defect means that a color has a higher density at a position on the filmstrip, where a sensitivity of a photosensitive material in each of the photosensitive layers has increased. The following are examples of possible causes increase in the sensitivity of the photosensitive material: an excessive pressure during rubbing and pressing the filmstrip, a fogging in static light or another light, a fogging by contacting with sensitizer-like material, faults of coating materials to vary densities thereof, and a fault of bases to vary densities thereof.

As the developed filmstrip is inspected with eyes for detecting of the defect, so much time is necessary for the inspection, and the determination whether the filmstrip has the defect is dependent on a subject of an inspector. Further, if the inspector is exhausted, he cannot carry out the precise determination. Especially, the coloring defect in yellow is more hardly found with eyes than that in red and blue.

The problem will be resolved if an inspection light is scanned on the filmstrip for the inspection. A light density of the inspection light becomes lower at an position of the coloring defect. However, a dust on the filmstrip makes it impossible to detect the defect with precision. Namely, as the dust diffuses the inspection light, the light density becomes lower at a position where there is dust on the filmstrip. Accordingly, it is hardly determined whether the decrease of the light density is caused by the defect or the dust. Further, the dust sometimes cannot be removed even if the cleaning of the filmstrip is carried out before the inspection.

SUMMARY OF THE INVENTION

An object of the present invention is to provide an inspection apparatus and an inspecting method for inspecting a light transmittable material to determine with high precision whether there is a coloring defect.

Another object of the present invention is to provide an inspection apparatus and an inspection method for detecting a coloring defect without decreasing the precision even if there is a dust on the filmstrip.

In order to achieve the object and the other object, an inspection apparatus includes at least one projector for projecting an inspection light to a position of a light transmittable material, and an auxiliary light projector for projecting an auxiliary light on to the position at another angle other than that of the inspection light. The auxiliary light, when there is a dust on the light transmittable material, is diffused by the dust. The inspection apparatus is provided with at least one light receiver whose number is the same as that of the projector. The light receiver is disposed on an optical axis of the projector and opposed thereto with the light transmittable material, and receives the inspection light and a part of the auxiliary light diffused by the dust. The receiving of the transmitted light causes the light receiver to generate a light receive signal and send it to a controller. In the controller a threshold of the light receive signal is memorized. If the light receive signal becomes lower than the threshold, it is determined that there is a defect in the light transmittable material. Further, the inspection apparatus includes a feed means for feeding the light transmittable material.

Further, the inspection apparatus is used for inspecting a continuous filmstrip in which different types of sample photo films are combined through joint members into the filmstrip. The inspection apparatus is provided with a joint member sensor and a film type sensor that generates discrimination signals for discriminating the joint members and the sample photo films respectively. The joint member sensor and the discrimination sensor separately send the discrimination signals to a light density adjusting device. The light density adjusting device adjusts the density of the inspection light in accordance with the discrimination signals such that the density of the transmitted light may be set to a predetermined level independent of the type of the photo film.

According to the invention, the density of the inspection light becomes lower at the position where the photo film has the defect. Further, the dust on the filmstrip diffuses the auxiliary light so as to tend a part of the auxiliary light onto the light receiver. Therefore the level of the density increases at the position of the dust, and the coloring defect can be detected with high precision.

BRIEF DESCRIPTION OF THE DRAWINGS

The above objects and advantages of the present invention will become easily understood by one of ordinary skill in the art when the following detailed description would be read in connection with the accompanying drawings.

PREFERRED EMBODIMENTS OF THE INVENTION

Figure 1:
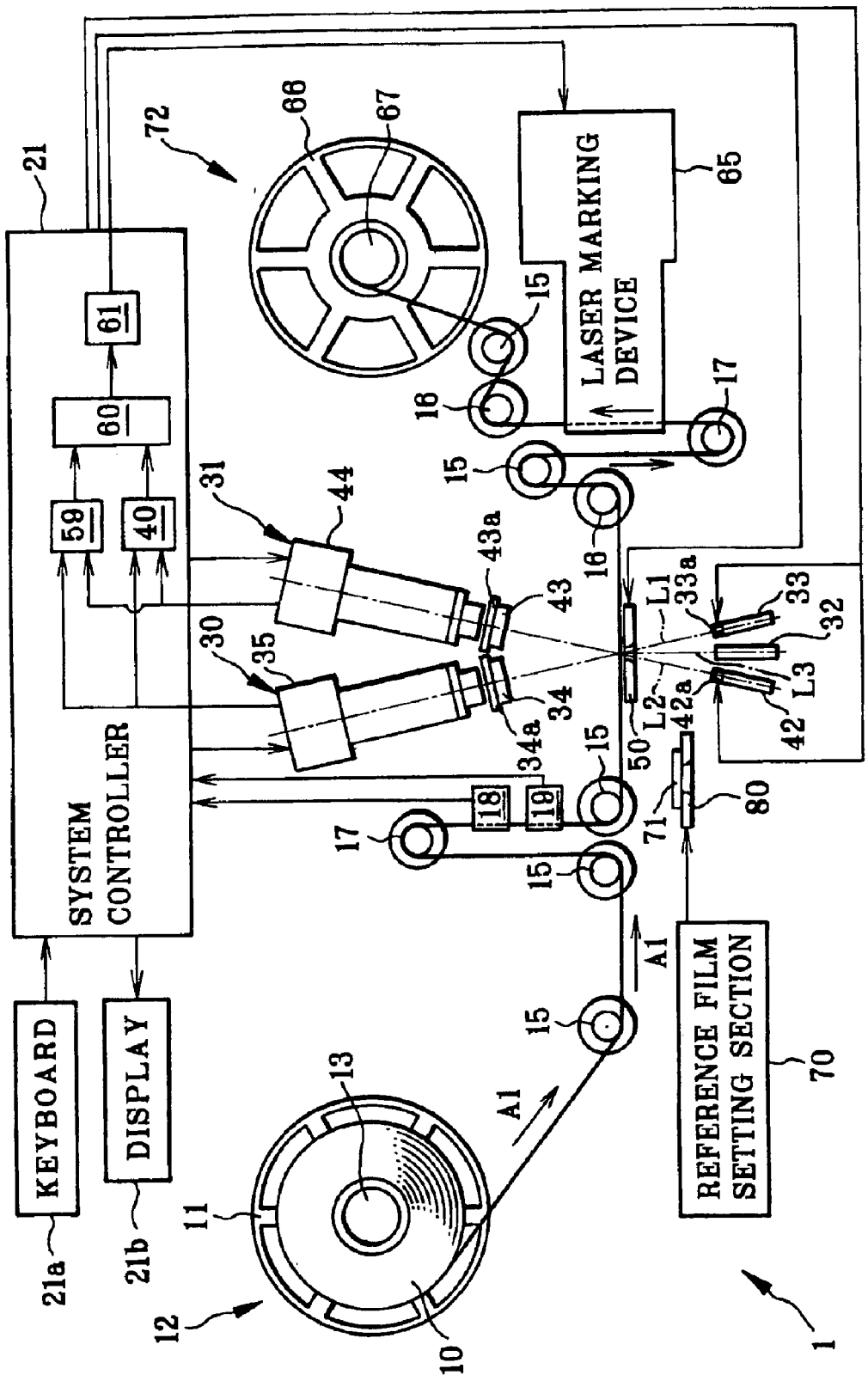
FIG. 1 is a schematic diagram of an inspection apparatus of the present invention.

As shown in FIG. 1, an inspection apparatus 1 includes a supply section 12, a splice sensor 18, a perforation sensor 19, an inspection stage 20, a controller 21, a first inspection light projector 33, a second inspection light projector 42, an auxiliary light projector 32, a first defect detector 30, a second defect detector 31, a marking device 65 and a take-up section 72. In the supply section 12, a filmstrip 10 is rolled about a reel 11, which is supported by a shaft 13. The filmstrip 10 is advanced in an advancing direction (or a scanning direction) Al with a guide roller 15, a roller 16, an intention adjusting roller 17 and the like, and sequentially fed to the splice sensor 18, the perforation sensor 19 and a film mask 50 of the inspection stage 20. Then, after passing through the marking device 65, the filmstrip 10 is taken-up around a reel 66 in the film take-up section 72. The splice sensor 18 and the perforation sensor 19 are connected to the controller 21, and respectively send thereto a splice discrimination signal for discriminating a splice 10a (see FIG. 2) and a perforation discrimination signal for discriminating perforations 22, 23 (see FIG. 2). When the filmstrip 10 is set on the film mask 50, the controller 21 controls the film mask 50 based on the splice discrimination signal and the perforation discrimination signals to determine an inspection area EA1, EA2 (see FIGS. 3A and 3B) on the filmstrip 10.

The first and second inspection light projectors 33, 42 project inspection lights on respective optical axes L1, L2 toward the filmstrip 10. The first defect detector 30 receives the inspection light on the optical axis L1 after transmitting the filmstrip 10, and the second defect detector 31 receives the inspection light on the optical axis L2 after transmitting the filmstrip 10. When receiving the inspection lights, the first and second defect detector 30, 31 generate data signals and send them to the controller 21. The data signals are analyzed in a judge section 40 and a position specifying section 60 which are included in the controller 21. Thereby the controller 21 controls stop sections 33a, 42a which are contained in the respective first and second inspection light projectors 33, 42 so as to adjust a density of the inspection light. When a coloring defect 8 (see FIG. 6B) is detected through the inspection, a defect data thereof is stored in a memory and thereafter sent to the marking device 65. The marking device 65 records at a position of the coloring defect 8 on the filmstrip 10 a mark indicating that the filmstrip has the defect, in accordance with receiving the defect data.

Note that roller pairs may be used so as to nip the filmstrip 10 instead of the guide roller 15, the roller 16, the intention adjusting roller 17.

Figure 2:
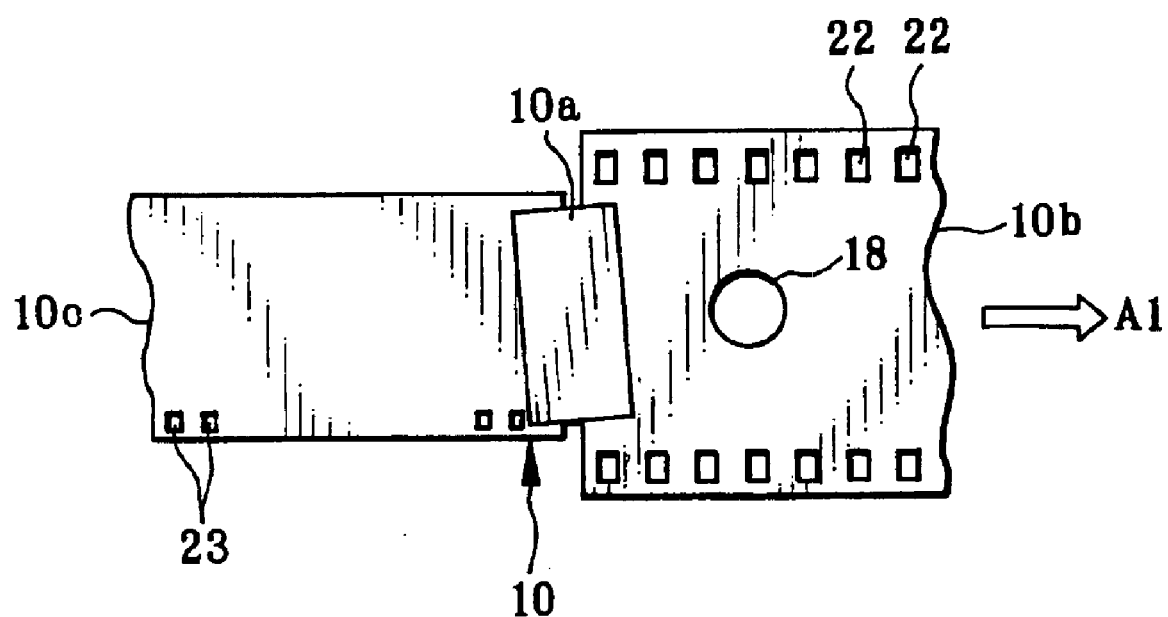
FIG. 2 is a plan view of a filmstrip to be inspected.

As shown in FIG. 2, in the filmstrip 10, sample films 10b and 10c are jointed with a light-shielding splice tape 10a. In the embodiment, the sample film 10b is a 135 type, and the sample film 10c is an IX 240 type. The splice sensor 18 includes a light emitter and a light receiver (not shown) confronting each other through the filmstrip 10. The light emitter emits a splice discrimination light onto the filmstrip 10. After transmitting the filmstrip 10, the splice discrimination light is received by the light receiver. Then the light receiver generates the splice discrimination signal. The splice discrimination signal varies when the splice tape 10a passes through the splice sensor 19. The controller 21 calculates a timing of passing of the splice tape 10a through the inspection stage 20, based on a pulse number of a signal sent from a film feed motor (not shown), and controls each section. The controller 21 is connected with a keyboard 21a and a display 21b which are used for input of information and operation.

Figure 3A:
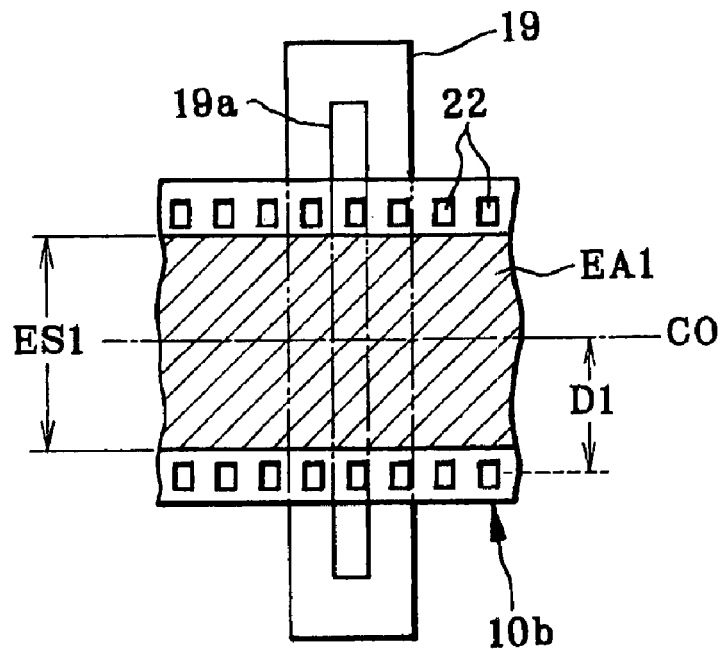
FIG. 3A is a plan view illustrating a positional relation between a sample photo film and a perforation sensor.
Figure 3B:
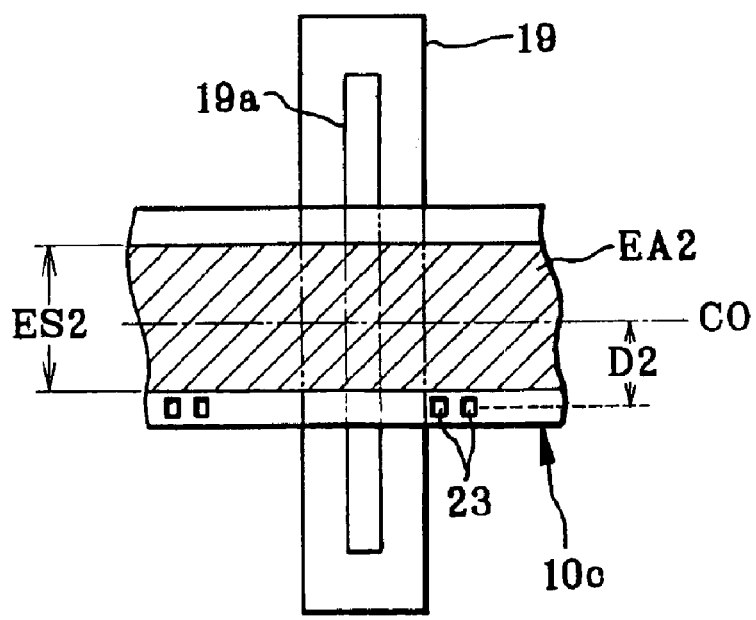
FIG. 3B is a plan view illustrating a positional relation between another sample film and the perforation sensor.

In FIGS. 3A and 3B, the perforation sensor 19 is constructed of a light emit section (not shown) and a light receive section 19a. The light receive section is constituted of a line CCD in which plural of light receive elements (not shown) are arranged in a line. The light emit section projects a perforation discrimination light through the filmstrip 10 toward the light receive section 19a. When perforations 22, 23 pass in the light, the density of the light varies on the light receive elements. The light receive section 19a generates the discrimination signal indicating the variation of the density of the perforation discrimination light, and sends the perforation discrimination signal to the controller 21.

The perforation discrimination signal indicates information about film types of the sample films 10b and 10c. For example, as shown in FIG. 3A, when the sample film 10b passes through the perforation sensor 19, the perforation discrimination signal indicates that perforations 22 are arranged at a predetermined interval in both edges at a distance D1 from a center C0 of the sample film 10b. Further, when the sample film 10c passes through the perforation sensor 19, the perforation indication signal indicates that perforations 23 are arranged at alternative intervals IA and IB in an edge at a distance D2 from the center C0.

Figure 4:
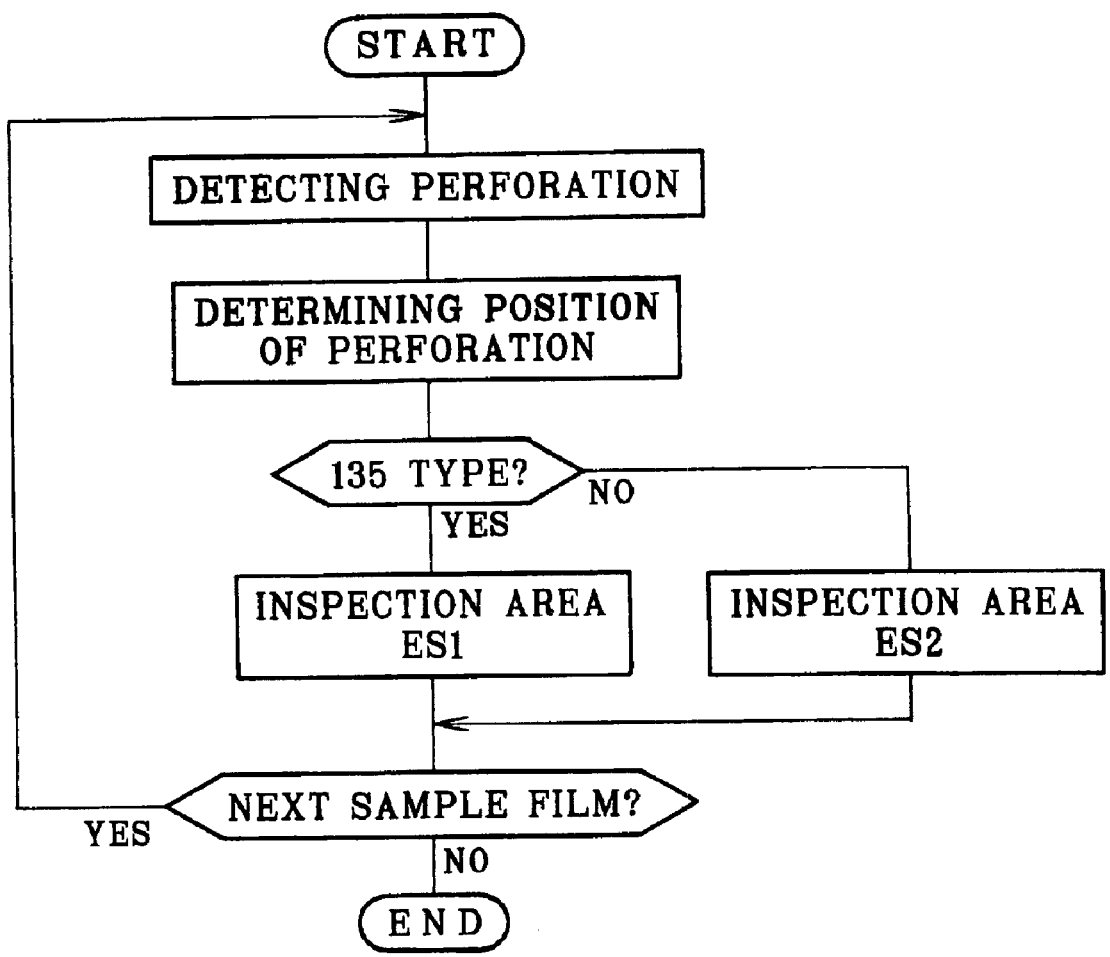
FIG. 4 is a flowchart illustrating steps and an order thereof for determining an inspection area on the photo film.

In the controller 21, data of the perforation discrimination signal according to a film type is memorized. For example, when the sample film is advanced, as shown in FIG. 4, the controller 21 discriminates the sample film 10b as the 135 film type based on the perforation discrimination signal, and thereafter determines an inspection area ES1 in image record area EA1. Further, when the sample film is advanced, the controller 21 discriminates the sampler film 10c as the IX 240 film type based on the perforation discrimination signal, and thereafter determines an inspection area ES2 in image record area EA2.

Figure 5:
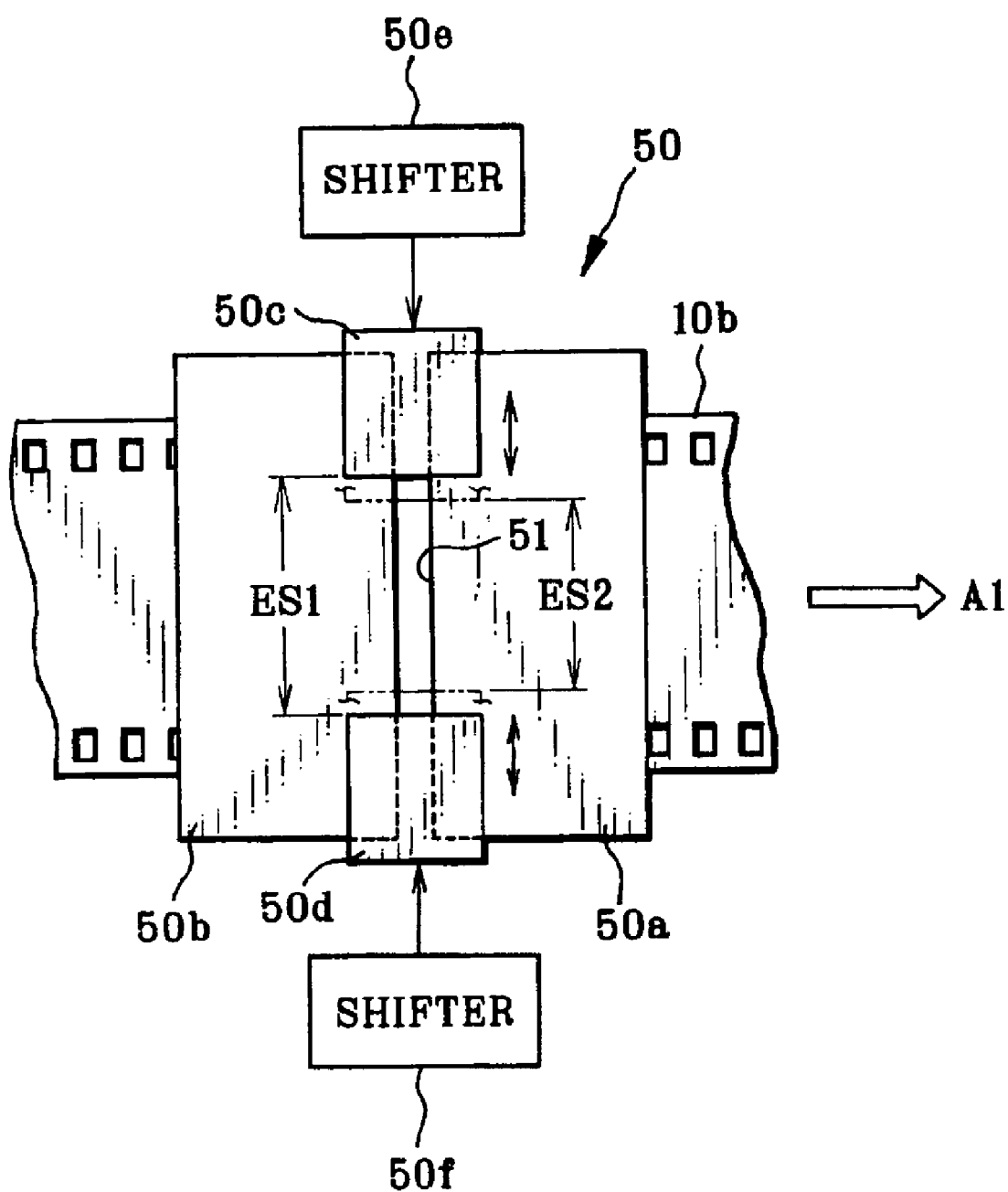
FIG. 5 is a plan view of a film mask in a situation in which an inspection area is determined.

As shown in FIG. 5, the film mask 50 of the inspection stage 20 is constituted of a pair of fixed masks 50a, 50b, a pair of movable masks 50c, 50d, and shifters 50e, 50f. The shifters 50e, 50f are controlled by the controller 21 and support the movable mask 50c, 50d so as to be movable to and from each other. Between the movable mask 50d, 50e is formed a mask opening 51 extending in the sub-scanning direction. A width of the mask opening 51 is set in accordance with determining the inspection areas ES1 and ES2.

Figure 6A:
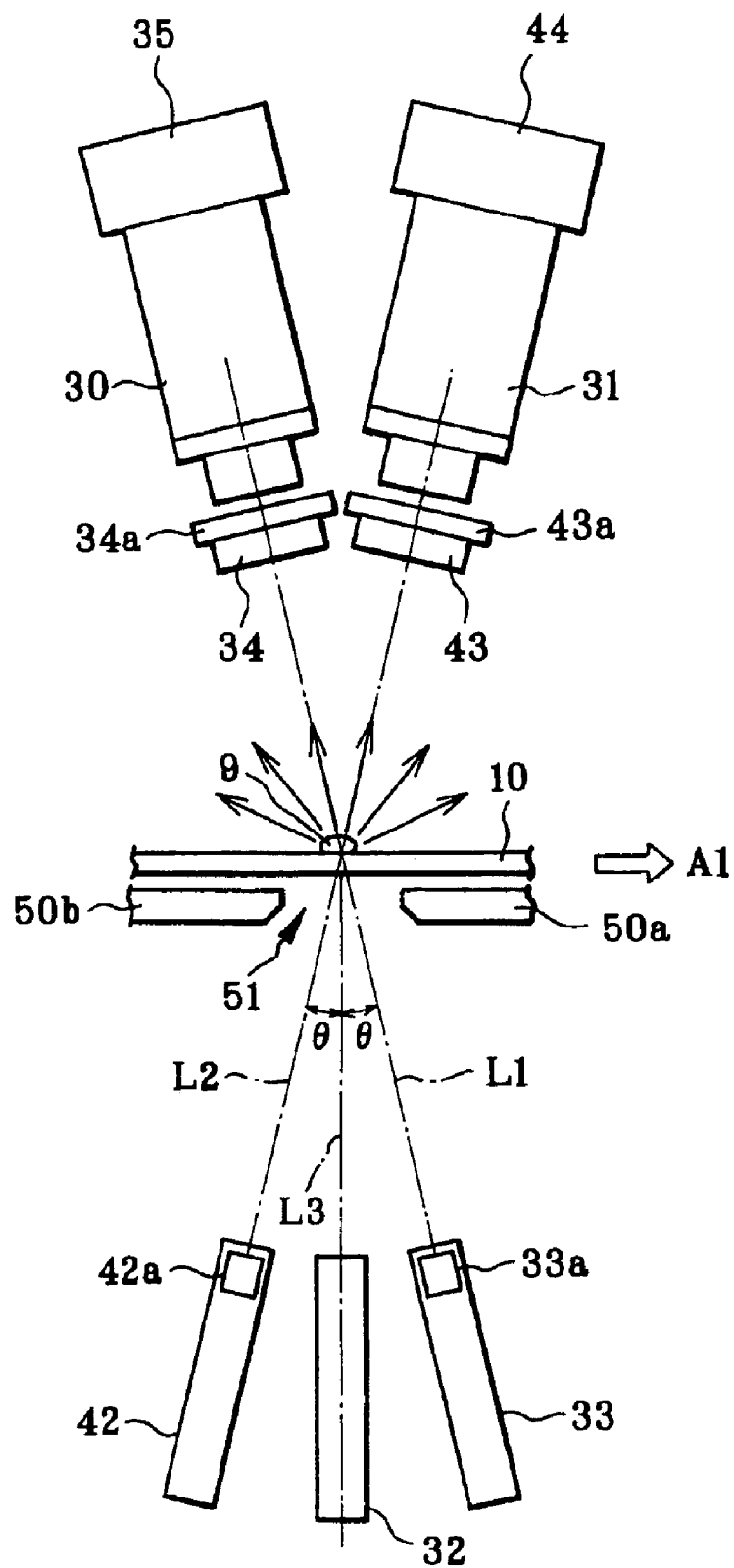
FIG. 6A is a plan view illustrating a situation in which the auxiliary light is diffused by the dust.
Figure 6B:
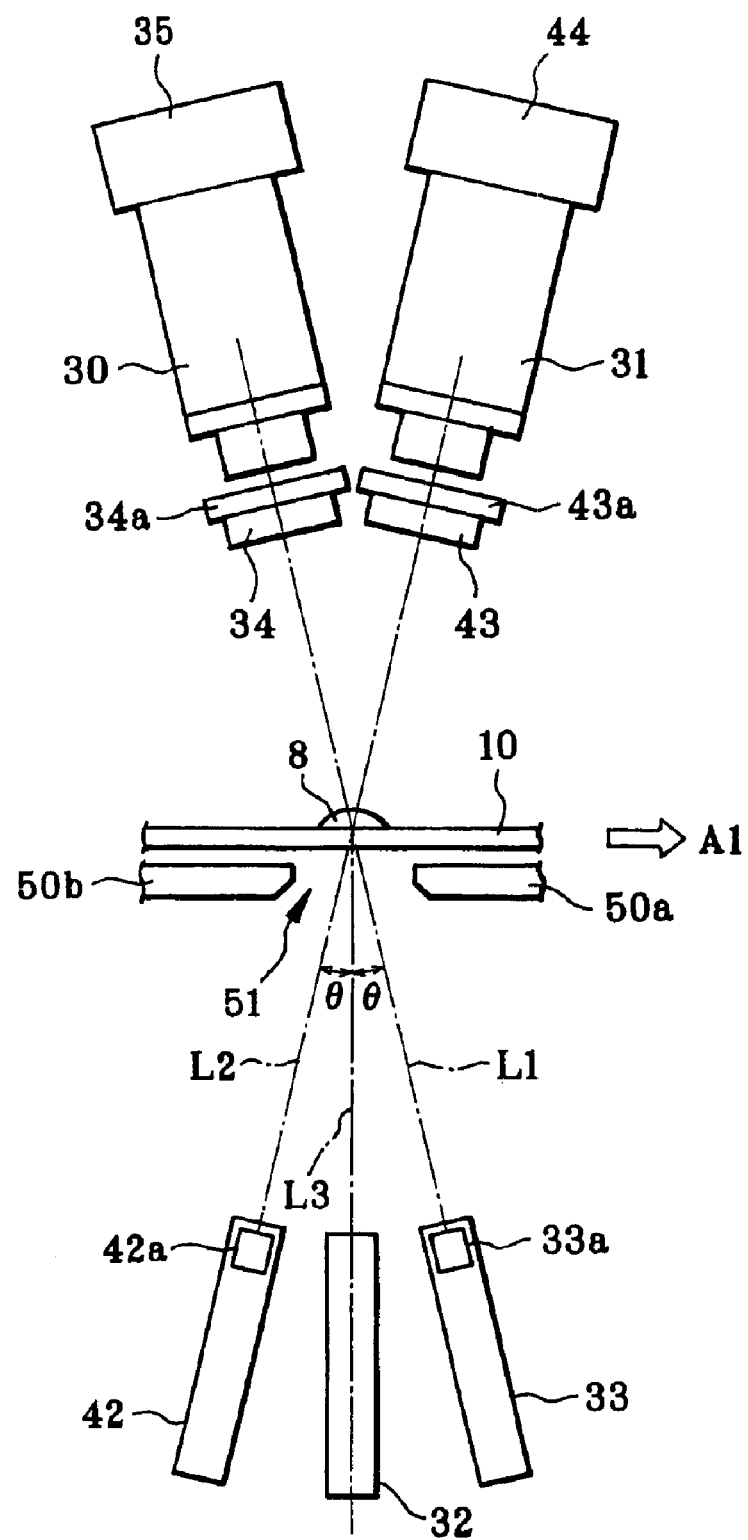
FIG. 6B is a plan view as same as FIG. 6A, wherein the sample photo film has a coloring defect.

As shown in FIGS. 6A and 6B, the auxiliary light projector 32 projects an auxiliary light on a optical axis L3 toward the filmstrip 10. Thereby the optical axis L3 crosses with the respective optical axis of the first and second inspection light projectors 33, 42 in a region of the filmstrip 10. Further, the optical axis L3 is perpendicular to a surface of the filmstrip 10, and the optical axes L1, L2 are set at the same incident angle θ to the optical axis L3 in both sides.

The filmstrip includes cyan, magenta and yellow coloring layers (not shown). The first defect detector 30 is used for detecting the coloring defect in the cyan and magenta coloring layers, and constructed of a filter 34, a light receive section 35. There are several types of the filter 34, and the most adequate type for detecting the coloring defect in the cyan and magenta coloring layers is used as the filter 34. The light receive section 35 includes a focusing lens and a line CCD (not shown). The inspection light projected by the first inspection light projector 33 transmits through the filmstrip 10. The inspection light is focused by the focusing lens on the line CCD. The line CCD outputs the data signal to be sent to the judge section 40.

The second defect detector 31 is used for detecting the coloring defect in the yellow coloring layer, and constructed of a filter section 43, a light receive section 44. There are several types of a filter 43a, and the most adequate type for detecting the coloring defect in the yellow coloring layer is used as the filter 43a. The light receive section 44 includes a focusing lens and a line CCD (not shown). The inspection light projected by the second inspection light projector 44 transmits through the filmstrip. The inspection light is focused by the focusing lens on the line CCD. The line CCD outputs the data signal to be sent to the judge section 40.

As shown in FIG. 6A, when there is a dust 9 at a position on the filmstrip 10, the inspection lights are diffused by the dust 9. However, the auxiliary light emitted from the auxiliary light projector 32 is also diffused by the dust 9. Accordingly, a part of the auxiliary light is received by one or both of the first and second defect detectors 30, 31, and a level of the data signal becomes higher at the position of the dust 9. As shown in FIG. 6B, when the filmstrip 10 has a coloring defect 8, the coloring defect 8 causes to decrease the density of the inspection light. Further, as not diffused by the coloring defect 8, the auxiliary light is tended neither to the first nor second defect detector 30, 31.

The judge section 40 determines whether the filmstrip 10 has the coloring defect 8, based on the signal data from the first and second defect detectors 30, 31. When the inspection light is projected on the filmstrip 10 without the dust 9 and the coloring defect 8, the data signal is detected at a predetermined level in the judge section 40. Note that in the present invention the level of the data signal is set to the predetermined one by controlling the stop device 33a, 42a of the controller 21, independent of the film type.

Figure 7:
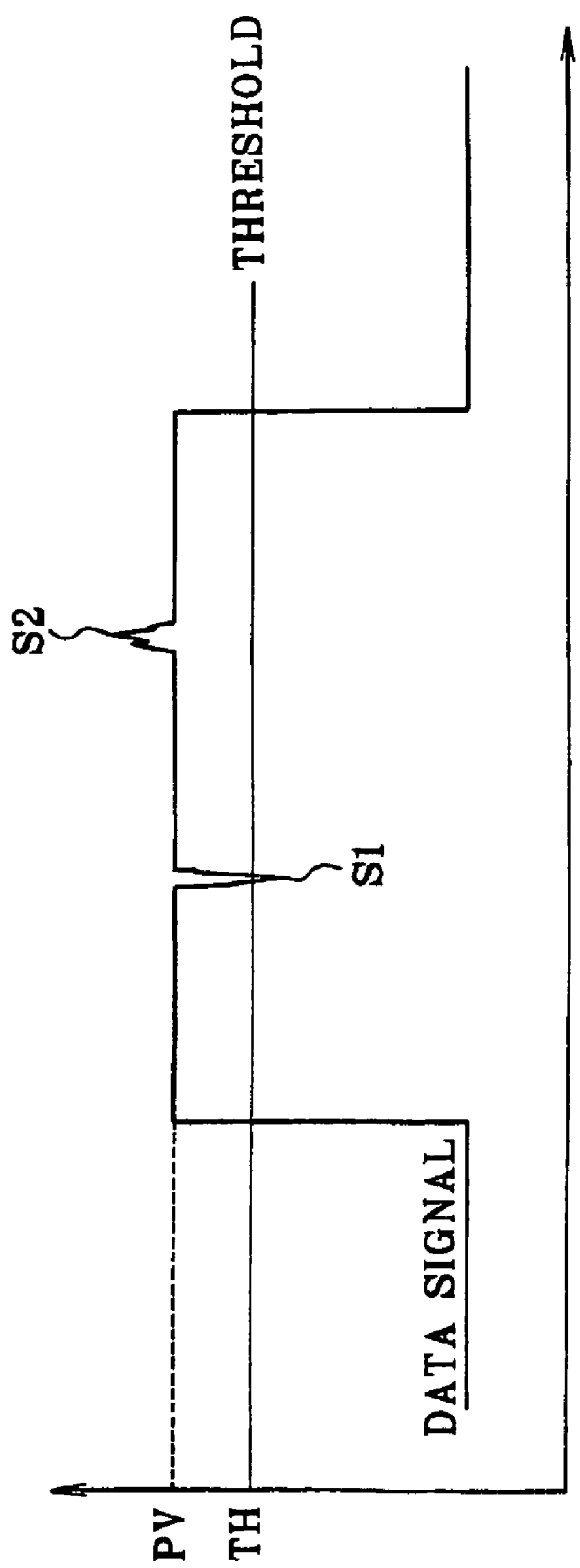
FIG. 7 is a graph illustrating a data signal and the threshold thereof.

As shown in FIG. 7, when the filmstrip 10 has the coloring defect 8, a signal S1 is detected under the predetermined level. Further, there is a threshold of the level of the data signal. If the level becomes under the threshold as the signal S1, the judge section 40 determines the filmstrip 10 has the coloring defect 8. When the dust lies on the filmstrip 10, the signal S2 higher than the predetermined level is detected.

Note that the data signal to be sent to the judge section 40 is not in form of an original data from each bit of the line CCD, but is transformed with a ran length method into a transformed data. The transformed data of the ran length method, as already known, describes a position and an amount of variation of the original data. Accordingly, the data signal is memorized from the transformed data in the memory. Therefore, not so much data is stored in the memory and the speed of operation becomes higher.

In FIG. 1, based on the data signal, the judge section 40 generates a defect signal and sends it to the position specifying section 60. The position specifying section 60 specifies from the defect signal the position and a type of the coloring defect 8, and a data of the position and the type is sorted in the memory 61. Note that, in the embodiment, the type of the coloring defect 8 is decided by a defect type discriminating section 59 in accordance with sizes of the coloring defect 8 categorized in three classes, for example, a large size defect, a middle size defect and a small size defect. The defect type discriminating section 59 analyzes a positional data in the data signal defect to detect a region in the coloring defect 8 where the density of the incident light does not change in the coloring defect 8, and categorizes the coloring defect 8 in accordance with a size of the area.

The marking device 65 is provided downstream of the inspection stage 20 in order to optically record a mark at the position of the coloring defect 8 by using a laser beam. There are three marks in accordance with categories of the coloring defect: a circle for the large size defect, a triangle for the middle size defect, and a tetragon for the small size defect. After recording of the mark, the filmstrip 10 is taken-up about a reel 66. Note that the mark may be recorded in another way than in use of the laser beam.

The inspection stage 20 is provided with a reference film setting section 70. The reference film setting section 70 sets, after moving the film mask 50, a reference film 71 on a film mask 80 when there is no filmstrip 10 on the film mask 50, for example, at the beginning of work and the setting of switch in an ON position. Then the inspection lights are projected on the reference film 71, read thereafter through the line CCDs in the first and second defect detectors 30, 31 for correcting each cell of the line CCD and carrying out a shading correction.

Effects of the present invention will be described now. The sample films 10b and 10c are joined with the splice tape 10a by using a splicer already known to form the filmstrip 10 having a length of several ten meters. The filmstrip 10 is rolled about the reel 11. The filmstrip 10 is processed with a film processor (not shown). After the processing, the filmstrip 10 is set in the supply section 12. Further, the filmstrip 10 is jointed by the splice tape 10a with a leader which is set in a film advancing path. Then a start key of the key board 21 is depressed to start the inspection, and the splice tape 10a of the filmstrip 10 is discriminated through the splice sensor 19. Further, perforations 22, 23 of the filmstrip 10 are detected through the perforation sensor 19. The position and the size of the perforations 22, 23 are used for discriminating the film type.

Just after the splice tape 10a reaches the mask opening 51, the film feed motor stops feeding the filmstrip 10. In this situation, the inspection lights and the auxiliary light is projected on the end of the filmstrip 10 to carry out the setting of the data signal of the density of the incident light to the predetermined value by controlling the stop devices 33a, 42a.

Then, the inspection area is determined based on the discrimination signals. Thereafter, the filmstrip 10 is fed at a predetermined velocity. When the filmstrip 10 has the dust 9 on a surface thereof, the auxiliary light is diffused with the dust 9, and as shown in FIG. 7, the signal S2 above the predetermined level is detected. Further, when the filmstrip 10 has the coloring defect 8, the signal S1 below the threshold is detected. As there is a difference from the signal S1 and signal S2, they can be easily discriminated. Accordingly, the coloring defect can be detected with high precision.

When the coloring defect 8 is detected, the data of the position and the type of the coloring defect 8 is stored in the memory 61. Based on the data in the memory 61, the marking device 65 selects the type of the mark to be printed on the filmstrip 10. After the marking device 65 records the mark at the position of the coloring defect 8 on the filmstrip, the filmstrip 10 is taken-up about the reel 66 in the film take-up section 72. When the filmstrip 10 is completely taken-up, the filmstrip 10 is removed from the shaft 67, and separated in the independent sample films. Based on the mark on the sample film, a matter of the coloring defect is investigated.

The embodiment includes two inspection light projectors and two defect detectors. However, in the present invention, the number of them may be one or more than three. For example, when the filmstrip having three coloring layer is inspected, three inspection light projectors and the three defect detector may be provided for respective coloring layers.

Instead of the inspection light, a laser beam may be scanned in the sub-scanning direction, as a device disclosed in Japanese Patent Laid-open Publication No. 6-207910. In such a case, a photoelectric transformation of the laser beam is carried out in the defect detector to generate the data signal.

The perforation sensor 19 may be constructed of plural light emit sections and light receive sections. In this case, they may be disposed at positions where the perforations of each film type pass. Further, in order to judge the film type, the splice sensor 19 may have a judging means. Furthermore, in the splice tape 10a, a bar code indicating the film type may be recorded. When the bar code is detected, information of bar code is read out, and the inspection area is determined. Furthermore, in the film mask 50, the width of the mask opening 51 is adjusted in accordance with the inspection area. In the present invention, cells in the line CCD of the light receive sections may be selectively driven corresponding to the inspection area.

Various changes and modifications are possible in the present invention and may be understood to be within the present invention.

What is claimed is:

1. An apparatus for inspecting a light transmittable material to detect a defect therein, comprising:

at least one inspection light projector for projecting an inspection light to a position on said light transmittable material;

an auxiliary light projector for projecting an auxiliary light toward said position;

at least one defect detector whose number is the same as that of said inspection light projector, for simultaneously receiving said inspection light and a part of said auxiliary light after transmitting through said light transmittable material to generate a light receive signal;

a judging device which receives said light receive signal from said defect detector, in which a threshold of a level of said light receive signal is memorized, said judging device comparing said light receive signal and said threshold to judge whether said light transmittable material has said defect.

2. An apparatus as claimed in claim 1, wherein said judging device judges whether said light transmittable material has said defect when said level becomes lower than said threshold of said light receive signal.

3. An apparatus as claimed in claim 2, further comprising a feed device for feeding said light transmittable material.

4. An apparatus as claimed in claim 3, wherein the respective number of said inspection light projector and said defect detector is at least two, optical axes of said projectors cross on said position of said light transmittable material, and said defect detectors each are disposed so as to respectively confront to said inspection light projectors through said light transmittable material.

5. An apparatus of claim 4, wherein said inspection light projectors and said auxiliary light projector are arranged along a scanning direction, and said auxiliary light projector is disposed between two of said projectors.

6. An apparatus of claim 5, wherein each number of said inspection light projectors and said defect detectors is at least two, and said auxiliary light projector is disposed such that an optical axis of said auxiliary light projector may divide into two equivalent parts an angular formed by two optical axes of said inspection light projectors.

7. An apparatus of claim 5, wherein said light transmittable material is a filmstrip in which plural types of sample films are jointed with a joint member.

8. An apparatus of claim 7, further comprising:

a joint member sensor for discriminating said joint member; and a film type sensor for discriminating said types of said sample films.

9. An apparatus of claim 8, further comprising an adjusting device for adjusting a density of said inspection light such that a density of said inspection light may be set to a predetermined level, independent of said type of said sample film.

10. An apparatus of claim 9, further comprising an inspection area determining section for determining an inspection area on said sample film to be inspected, based on discrimination signals generated in said joint member sensor and said judge sensor.

11. The apparatus according to claim 1, wherein the judging device compares the light receive signal to a level reference, and wherein areas where the receive light exceeds the level reference corresponds to a first form of defect and wherein areas where the receive light is lower than the threshold correspond to a second form of defect.

12. The apparatus according to claim 11, where in the level reference and threshold each maintain a constant respective value for a frame of image stored to the light transmittable material.

13. The apparatus of claim 4, wherein a first inspection light and detector corresponds to sensitivities of a first color and a second inspection light and detector correspond to sensitivities of a second color.

14. The apparatus of claim 13, wherein the second color is yellow.

15. The apparatus of claim 1, further comprising a size indication for the defect based on results of the judging device.

16. A method of inspecting a light transmittable material to detect a defect therein, comprising the steps of:

feeding said light transmittable material by a feed device;

projecting an inspection light and an auxiliary light such that said inspection light and said auxiliary light may cross on said light transmittable material, said auxiliary light being diffused by a dust when said dust lies on said light transmittable material;

simultaneously receiving said inspection light and a part of said auxiliary light by a defect detector after passing through said light transmittable material;

photoelectrically transforming said inspection light and said part of said auxiliary light to generate a data signal;

comparing said data signal with a threshold to determine that said light transmittable material has said defect.

17. A method of claim 16, wherein said light transmitting material is a continuous filmstrip in which several types of sample films are jointed by a joint member, said method comprising the steps of:

discriminating a film type by a film type sensor;

determining an inspection area on said filmstrip corresponding to said film type.

* * * * *